United States Patent [19]
Bunker et al.

[11] Patent Number: 4,544,467
[45] Date of Patent: Oct. 1, 1985

[54] LIGHT-CURABLE DENTIN AND ENAMEL ADHESIVE

[75] Inventors: James E. Bunker; Richard P. Fields, both of St. Paul, Minn.

[73] Assignee: Minnesota Mining and Manufacturing Company, St. Paul, Minn.

[21] Appl. No.: 508,807

[22] Filed: Jun. 28, 1983

[51] Int. Cl.[4] .......................... C08J 3/28; C08L 85/02
[52] U.S. Cl. .......................... 204/159.24; 204/159.23; 433/217.1; 433/222.1; 433/228.1; 523/109
[58] Field of Search .................. 204/159.23, 159.24; 433/228, 212, 222, 217; 523/109

[56] References Cited

U.S. PATENT DOCUMENTS

| | | | |
|---|---|---|---|
| 3,066,112 | 11/1962 | Bowen | 260/41 |
| 3,709,866 | 1/1973 | Waller | 260/27 R |
| 3,759,807 | 9/1973 | Osborn et al. | 204/159.23 |
| 3,827,956 | 8/1974 | McGinniss | 204/159.23 |
| 3,827,957 | 8/1974 | McGinniss | 204/159.23 |
| 3,827,958 | 8/1974 | McGinniss | 204/159.23 |
| 3,926,643 | 12/1975 | Chang | 96/115 P |
| 4,071,424 | 1/1978 | Dart | 204/159.15 |
| 4,089,762 | 5/1978 | Fredsham | 204/159.15 |
| 4,110,184 | 8/1978 | Dart et al. | 204/159.23 |
| 4,182,035 | 1/1980 | Yamauchi et al. | 433/228 |
| 4,222,780 | 9/1980 | Shibatani et al. | 106/35 |
| 4,235,633 | 11/1980 | Tomioka et al. | 106/35 |
| 4,259,075 | 3/1981 | Yamauchi et al. | 433/217 |
| 4,259,117 | 3/1981 | Yamauchi et al. | 106/35 |
| 4,350,532 | 9/1982 | Randklev | 106/30 |
| 4,368,043 | 1/1983 | Yamauchi et al. | 433/217 |

FOREIGN PATENT DOCUMENTS

| | | |
|---|---|---|
| 0037677 | 10/1981 | European Pat. Off. . |
| 0058483 | 8/1982 | European Pat. Off. . |
| 0059649 | 9/1982 | European Pat. Off. . |
| 0070634 | 1/1983 | European Pat. Off. . |
| 3133008 | 4/1982 | Fed. Rep. of Germany ...... 523/109 |
| 56-120610 | 9/1981 | Japan . |
| 57-143372 | 9/1982 | Japan . |
| 57-167364 | 10/1982 | Japan . |

OTHER PUBLICATIONS

Anbar, M. and E. Farley, *J. Dent. Res.*, 53, 879 (1974).
Bowen, R. L., En. N. Cobb, and L. E. Setz, *Dentistry*, 82, 11 (Dec. 1982).
Bowen, R. L., E. N. Cobb and J. E. Rapson, *J. Dent. Res.*, 61, 1070 (1982).
Buonocore, M. and M. Quigley, *J. Amer. Dent. Assoc.*, 57, 807 (1958).
Buonocore, M., W. Wileman, and F. Brudevald, *J. Dent. Res.*, 35, 846 (1956).
Farley, E., R. Jones, and M. Anbar, *J. Dent. Res.*, 56, 1943 (1977).
Hirasawa et al., "Physical Properties of Polymethyl Methacrylates Filled with Silica Gel For Dental Materials", *Reports of the Institute for Medical & Dental Engineering*, 2, 62–66 (1968).

*Primary Examiner*—Allan M. Lieberman
*Attorney, Agent, or Firm*—Donald M. Sell; James A. Smith; David R. Cleveland

[57] ABSTRACT

Light-curable dentin and enamel adhesives comprising phosphorus-containing polymerizable monomer, sulfur compound having sulfur in the $+2$ or $+4$ oxidation state, selected photoinitiators, and an optional peroxide compound, as well as one-step and two-step curing methods.

15 Claims, No Drawings

LIGHT-CURABLE DENTIN AND ENAMEL ADHESIVE

TECHNICAL FIELD

This invention relates to light-curable compositions useful in dentistry. This invention also relates to a method for repairing, adhering to, or altering the position of teeth, through the use of such compositions.

BACKGROUND ART

Practitioners in the field of dentistry have long sought polymerizable compositions which would adhere well to dentin. A number of compositions having varying degrees of adhesion to dentin have been reported in the literature, see, e.g., M. Buonocore, W. Wileman, and F. Brudevold, *J. Dent. Res.*, 35, 846 (1956), M. Buonocore and M. Quigley, *J. Amer. Dent. Assoc.*, 57, 807 (1958), M. Anbar and E. Farley, *J. Dent. Res.*, 53, 879 (1974), E. Farley, R. Jones, and M. Anbar, *J. Dent. Res.*, 56, 1943 (1977), R. L. Bowen, E. N. Cobb, and J. E. Rapson, *J. Dent. res.*, 61, 1070 (1982), R. L. Bowen, E. N. Cobb, and L. E. Setz, *Denistry* 82, 11 (December 1982), U.S. Pat. Nos. 4,182,035, 4,222,780, 4,235,633, 4,259,075, 4,259,117, and 4,368,043, European published patent application No. 0 058 483, and Japanese laid-open patent application (Kokai) Nos. 57-143372 and 57-167364. These compositions generally are used in the form of primers or liners which are applied to dentin in one or more thin coats followed by application of a dental composite, restorative, or adhesive composition to the primer-coated dentin surface.

In recent years, one-part visible light cure compositions have become popular in dentistry, particularly in connection with dental composite, restorative, and adhesive compositions, as these compositions typically are highly loaded with fillers and are difficult to mix with chemical cure polymerization initiators. There has been no particularly pressing need for one-part visible light cured dentin primers, since such primers are low viscosity liquids containing little or no filler content, and can be readily dispensed, mixed, and used in conventional two-part chemical cure formats. There has been relatively little discussion in the literature of visible light cure dentin primers, exceptions being the above-mentioned European patent application No. 0 058 483 (which describes a light-cured dentin primer containing photoinitiators "such as monoketals of aromatic 1,2-diketones or a combination of benzil and a dialkylamino acrylate or methacrylate"), and Japanese laid-open patent application No. 56-120610 (abstracted in *Chem. Abs.*, 95, 225704u (1981)), and said to describe a resin mixture containing diglycidyl methacrylate of Bisphenol A (also known as "BIS-GMA"), triethylene glycol dimethacrylate and 2-methacryloxyethyl phenyl phosphate, which mixture is polymerized in the presence of camphoroquinone and allylthiourea.

Many references describe one-part visible light cure compositions which contain fillers and are suitable for use in dentistry, including U.S. Pat. Nos. 3,709,866 and 4,110,184, and European published patent application Nos. 0 059 649, 0 058 483, and 0 070 634. Other visible light cure compositions said to have more general utility (e.g., as paints or coatings) are disclosed in U.S. Pat. Nos. 3,759,807, 3,926,643, 4,071,424, and 4,089,762. Most of the visible light cure compositions exemplified in the above-mentioned references contain an amine compound which facilitates photopolymerization. Some of the above-mentioned references suggest other compounds which can be used in place of an amine; one reference (U.S. Pat. No. 4,110,184) mentions (without exemplifying) the use of "soluble salts of aromatic sulfinic acids" in place of amines in a filler-loaded visible light cure dental composition.

DISCLOSURE OF INVENTION

The present invention provides, in one aspect, two-part visible light cure dentin and enamel primer compositions. When said two parts are mixed, said compositions comprise:

(a) phosphorus-containing free-radically polymerizable monomer suitable for use in the oral environment;

(b) sulfur compound having sulfur in the $+2$ or $+4$ oxidation state; and (c) Photoinitiator selected from substituted (e.g., with lower ($C_{1-4}$) alkyl, substituted alkyl, alkoxy, halogen, or nitro) and unsubstituted alkylphenones, substituted (e.g., with lower ($C_{1-4}$) alkyl, unsubstituted alkyl, alkoxy, halogen, or nitro) and substituted benzilidene acetophenones, and compounds of the formula:

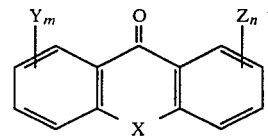

wherein:
X is nothing (i.e., not bond), a carbon-carbon bond, $>CR_2$, $>C=R^1$, $>C=O$, $>S$, $>SO$, $>SO_2$, $>O$, or $>NR$ where each R is independently H or a lower ($C_{1-4}$) alkyl or substituted alkyl group and $R^1$ is a tetravalent unsaturated aliphatic radical doubly bonded to said C of $>C=R^1$ and bonded to the 4 or 5 position of said Formula I to form a fused ring structure;

Y and Z are independently lower ($C_{1-4}$) alkyl, substituted alkyl (e.g., —$CF_3$), a divalent unsaturated radical bonded to adjacent positions of said Formula II to form a fused ring structure, alkoxy, halogen, or nitro; and m and n are independently zero to 4.

The present invention also provides a method for using such compositions to repair or veneer hard dental tissue, and a method for applying orthodontic brackets or crowns to hard dental tissue using said compositions.

The compositions of the invention are two-part visible light cure compositions, in contrast to typical light cure compositions which are packaged as one-part systems. Two-part packaging is used in the present invention since the sulfur compound (viz., component (b), above) tends to promote homopolymerization of the phosphorus-containing polymerizable monomer (viz., component (a), above) if components (a) and (b) are stored together. The two parts (one part containing component (a), the other part containing component (b), and one or both parts containing component (c)) are mixed together just prior to use, applied to dentin or enamel, and irradiated with a conventional visible light source. Although the use of a two-part visible light cure composition may seem to be a step backward from the standpoint of convenience (since an ordinary two-part chemical cure composition would be just as easily mixed and would not require use of a curing light), the compositions of the invention nonetheless represent a significant advance. The compositions of the invention exhibit markedly greater adhesion to dentin and enamel than corresponding two-part chemical cure compositions cured with chemical cure systems (e.g., peroxide-amine cure systems). The dentin-primer bond formed with compositions of the invention is sufficiently strong that cohesive failure of dentin has been observed during shear strength tests (for example, chunks of dentin have been ripped from test teeth during in vitro shear strength testing).

DETAILED DESCRIPTION

In the practice of the present invention, the phosphorus-containing polymerizable monomer (component (a)) is a monomer or mixture of monomers (or mixture thereof with a suitable diluent) having sufficiently low viscosity to enable the compositions of the invention to be applied readily to exposed tooth surfaces using, e.g., a small brush or dropper. Suitable polymerizable monomers should be safe for use in the oral environment, both in their unpolymerized and polymerized state, typically, the polymerizable monomer contains one or more olefinically unsaturated groups. The polymerizable monomer can be selected by combining it with a conventional peroxide-amine chemical cure system (using 2 weight percent benzoyl peroxide and 1 weight percent dihydroxyethyl para-toluidine) and evaluating the ability of the resulting mixture to bond to tooth structure and to conventionally-used polymerizable dental materials (e.g., composites, restoratives, or adhesives). Such evaluation can be carried out using the shear strength test recited in Example 1 of said European published patent application No. 0 058 483. Suitable polymerizable monomers will exhibit an average measured shear strength on unetched dentin of at least 5 kg/cm$^2$, and preferably at least 20 kg/cm$^2$.

Preferred polymerizable monomers for use in the present invention are monomers containing phosphorus atoms bonded (through a P—O—C or P—C linkage) to one or more olefinically unsaturated groups and bonded to one or more chlorine atoms (through a P—Cl linkage), bromine atoms (through a P—Br linkage), active hydrogen atoms (through a P—O—H linkage), or alkyl, substituted alkyl, allyl, or substituted allyl groups (through a P—O—C linkage). A particularly preferred class of polymerizable monomer is the phosphorus acid esters described in said European published patent application No. 0 058 483, such class containing compounds comprising an organic ester of one or more acids of phosphorus, the organic radical of said ester containing at least one free-radically polymerizable functional group, wherein said ester has chlorine or bromine bonded directly to phosphorus (hereafter referred to as "halophosphorus acid esters"). An especially preferred subclass of such halophosphorus acid esters is halophosphorus acid esters wherein said organic radical is the residue remaining after removal of one or more hydroxyl hydrogen atoms from BIS-GMA, particularly those wherein phosphorus is doubly bonded to an oxygen atom, is bonded to at least one chlorine atom, and the ratio of said phosphorus to said BIS-GMA is between about 0.025:1 and 1:1.

An additional preferred subclass of polymerizable monomer for use in the present invention is the phosphorus acid esters described in said U.S. Pat. Nos. 4,182,035, 4,222,780, 4,235,633, 4,259,075, 4,259,117, and 4,368,043. An especially preferred member of such subclass is the compound 2-methacryloxyethyl phenyl phosphate.

A further preferred subclass of polymerizable monomers for use in the present invention is the pyrophosphate ester derivatives described in said Japanese laid-open patent application Nos. 57-143372 and 57-167364.

A further preferred polymerizable monomer is glycerophosphate dimethacrylate, as described in said Bounocore, Wileman, and Brudevold reference.

The polymerizable monomers can be used alone or in mixtures. If desired, other free-radically polymerizable non-phosphorus containing monomers can be mixed therewith, for example, as a diluent to control viscosity or assist wetting. Suitable other free-radically polymerizable monomers include acrylates and methacrylates such as triethyleneglycol dimethacrylate, neopentylglycol dimethacrylate, pentaerythritol tetracrylate, hexamethyleneglycol diacrylate, and trimethylolpropane trimethacrylate.

The polymerizable monomers (hereinafter, the phrase "polymerizable monomer" will be used to refer to said phosphorus-containing polymerizable monomers) can be prepared using methods known to those skilled in the art, as shown, e.g., in said European published patent application No. 0 058 483 and in the patents cited therein. For example, especially preferred halophosphorus esters can be prepared by combining BIS-GMA in a diluent with about 0.25 to 10 percent by weight (based on the weight of BIS-GMA) phosphorus oxychloride and allowing the resulting mixture to stand at room temperature until the viscosity of the mixture reaches a stable equilibrium.

Preferably, the polymerizable monomer is about 5 to 95 percent of the weight of compositions of the invention. In general, the weight of other components of such compositions can be determined by reference to the weight of polymerizable monomer therein.

The sulfur compound having sulfur in the $+2$ or $+4$ oxidation state (component (b) above) acts as a polymerization for the polymerizable monomer, and enhances adhesion of the compositions of the invention to dentin. The sulfur compound can be selected by dissolving it in a suitable solvent (e.g., ethanol) at 3 percent by weight, adding the resulting solution to the polymerizable monomer mixture of Example 1 of said European published patent application No. 0 058 483 and carrying out the shear strength that recited therein. Suitable sulfur compounds will exhibit an average measured shear strength on unetched dentin of at least 5 kg/cm$^2$, and preferably at least 20 kg/cm$^2$.

Preferred sulfur compounds are alkali metal salts (such as potassium or sodium salts), or ammonium salts of sulfur-containing anions such sulfinate, sulfite, sulfonate, bisulfite, metabisulfite, or hydrosulfite anions, or the free acid counterparts thereof. Suitable sulfur compounds include sodium benzene sulfinate, sodium para-toluene sulfinate, ammonium sulfonate, tetrabutylammonium bisulfite, potassium metabisulfite, para-toluene sulfinic acid, and the like, or mixtures thereof. Sodium benzene sulfinite and sodium para-toluene sulfinate are preferred sulfur compounds.

The sulfur compound generally is present in compositions of the invention (after mixture thereof) in amounts of about 1 to 20% by weight, preferably about 2 to 10% by weight, based on the weight of said polymerizable monomer. The sulfur compound typically is dissolved in a suitable solvent, such as water, acetone, or ethanol, or mixtures thereof.

The photoinitiator (component (c) above) acts as a source of free radicals when compositions of the invention are exposed to light in the visible and near-visible portions of the spectrum (viz., light with a wave length between about 300 and 500 nanometers). In general, the photoinitiator is a yellow or pale yellow liquid or solid when in pure form. The photoinitiator can be selected by examining the color of the photoinitiator (both in pure form and when the photoinitiator is dissolved in a suitable solvent such as ethanol) and selecting photoinitiators which have pale yellow or yellow coloration. Absence of yellow coloration is indicative of weak photoinitiating activity. Strong yellow coloration can be undesirable since the photoinitiator may impart an overall yellow coloration to cured compositions of the invention, and, in thick films, can promote cure of the surface of the thick film proximate the light source and undercure of the remainder of such thick film.

Preferred photoinitiators include alkyl phenones, benzilidene acetophenones (viz., chalcones), and compounds in which X in Formula I above is nothing (viz., benzophenones), a carbon-carbon bond (viz., fluorenones), $>CH_2$ (viz., anthrones), $>CR^2$ where $R^2$ is the radical $=CHCH=CH-$ bonded to the 5 position of Formula 1 to form a fused ring structure (viz., benzanthrones), $>C=O$ (viz., anthraquinones), $>S$ (viz., thioxanthones), $>SO$ (viz., thioxanthone oxides), $>SO_2$ (viz., thioxanthone dioxides), $>O$ (viz., xanthones), or $>NR$ (viz., acridones). Preferred photoinitiator substituents include chloro groups, lower alkyl groups (e.g., isopropyl groups), trifluoromethyl groups, and nitro groups. Representative photoinitiators include acetophenone, chalcone, benzophenone, 9-fluorenone, anthrone, benzanthrone, anthraquinone, benzanthraquinone, thioxanthrone, 2-chlorothioxanthone, 2-isopropylthioxanthone, 2-nitrothioxanthone, 2-chloro-7-trifluoromethylthioxanthone, thioxanthone-10-oxide, 2-chlorothioxanthone-10,10-dioxide, xanthone, 2-chloroxanthone, 4-bromoxanthone, and 10-methyl-9-(10H)acridone. Other suitable photoinitiators are listed in said U.S. Pat. No. 3,759,807.

Preferably, the photoinitiator is a xanthone or thioxanthone, particularly 2-chlorothioxanthone.

The photoinitiator is present in the compositions of the invention (after mixture thereof) in amounts of about 0.05 to 5% by weight, preferably about 0.1 to 0.5% by weight, based on the weight of said polymerizable monomer. The amount of photoinitiator should be sufficient to provide the desired rate of cure and overall physical properties, while minimizing yellow coloration of the composition of the invention after cure.

In a preferred embodiment of the invention, one or more peroxide compounds are added to compositions of the invention. Peroxide compounds facilitate polymerization and enhance adhesion of compositions of the invention to dentin. Suitable peroxide compounds include acyl and acyl peroxides and hydroperoxides and diacyl and dialkyl peroxides, such as benzoyl peroxide, t-butyl hydroperoxide, acetyl peroxide, lauroyl peroxide, and the like. Benzoyl peroxide is a preferred peroxide compound. Peroxide compounds can be present in compositions of the invention in amounts of about 0.05 to 10 percent by weight, preferably about 0.5 to 2 percent by weight, based on the weight of said polymerizable monomer.

Basic compounds (including amines) can be added to compositions of the invention if desired, and will serve to neutralize acids (e.g., HCl) which may be present in the compositions of the invention before or after polymerization. Suitable basic compounds include potassium hydroxide, dihydroxyethyl para-toluidine, triphenylamine, and the like. Basic compounds can be added in an amount sufficient to provide the desired degree of acid neutralization.

Other adjuvants such as diluents, solvents, stabilizers, fillers, pigments, indicators, inhibitors, and the like can also be used in compositions of the present invention. The amounts and types of such adjuvants, and their manner of addition to the compositions of this invention, will be essentially the same as currently used in existing dentin primer compositions familiar to those skilled in the art.

In an additional embodiment of the invention, filler-containing two-part visible light cure compositions can be made using fillers such as silane-treated quartz (see, e.g., U.S. Pat. No. 3,066,112), microfine silica (see, e.g., Hirasawa et al., "Physical Properties of Polymethyl Methacrylates Filled With Silica Gel For Dental Materials", *Reports of the Institute for Medical & Dental Engineering,* 2, 62–66 (1968)), radiopaque zinc glass (see, e.g., U.S. Pat. No. 4,350,532), calcium hydroxide or other radiopaque fillers, pulverized chip polymers (e.g., filled or unfilled particles of polymerized methyl methacrylate), asbestos-free talc or other low Mohs hardness filler (see, e.g., European published patent application No. 0 037 677) and other fillers known to those skilled in the art. Such filler-containing compositions are useful as cavity liners, restoratives, composites, and adhesives.

Compositions of the invention preferably are put up in two-part packages. The polymerizable monomer and sulfur compound are kept separate until use. The photoinitiator can be packaged with either the polymerizable monomer or the sulfur compound or with both the polymerizable monomer and the sulfur compound.

In a preferred package, the polymerizable monomer is combined with any desired diluents (if used) and a peroxide compound to form a first part. The sulfur compound and photoinitiator are dissolved in a suitable solvent (e.g., ethanol) to form a second part. While uncombined, the resulting two-part package will remain in a stable, uncured state. When the two parts are mixed together (e.g., by spatulation, stirring, or other means) and exposed to a sufficient quantity and intensity of visible light, the resulting mixture will rapidly cure. The amount of each ingredient in such two-part package should be adjusted to allow sufficient working time for the practitioner to mix, apply, and irradiate the composition as desired, coincident with attainment of the desired physical properties in the cured composition.

If desired, other combinations of polymerizable monomer, sulfur compound, photoinitiator, peroxide (if used) and any other desired adjuvants can also be employed in two-part packages of compositions of this invention. Preferably, such packages offer ease of mixing, good shelf life, and desirable physical properties after cure.

When used as dentin primers, the compositions of this invention are applied in a manner similar to that used for existing dentin primer compositions. Excavation can be limited to the removal of damaged or defective tooth structure. Undercutting of the cavity generally is not required. Preferably, enamel margins (if present) are acid-etched using conventional etchants, but acid etching of dentin is avoided. In a preferred method of the invention, enamel margins (if present) are etched with a conventional etchant, one or more thin layers of the compositions are applied to the etched enamel and exposed dentin, and the layer(s) are exposed to a sufficient quantity and intensity of visible light to harden the composition. Each layer can be exposed separately if desired. Next, a visible light cure composite, restorative, or adhesive composition is applied to the hardened layer(s) and exposed to visible light until cured. This procedure (hereafter referred to as a "two-step" curing method) usually provides much stronger primer-dentin bonds than are obtained using "one-step" curing of a composite, restorative, or adhesive composition without precure of underlying primer.

When used as a cavity liner or crown preparation, the compositions of the invention preferably are applied in one or more layers. Each layer should be exposed to a sufficient quantity and intensity of visible light to harden the layer.

When used as a composite, restorative, or adhesive, the compositions of the invention are used in a fashion similar to that used for existing visible light cure composites, restoratives, and adhesives. Preferably, such compositions are used in conjunction with a dentin primer and cavity liner or crown preparation prepared according to this invention.

The following examples are offered to aid understanding of the present invention and are not to be construed as limiting the scope thereof.

EXAMPLE 1

Preparation of Fre-Radically Polymerizable Monomer

A refrigerated resin mixture containing 237.5 g BIS-GMA, 237.5 g triethyleneglycol dimethacrylate, 0.314 g butylated hydroxytoluene and 0.0475 g hydroquinone methyl ether was stirred in a flask with 25 g phosphorus oxychloride for three hours while keeping the temperature of the reaction mixture below 24° C. with an ice bath. The reaction mixture was allowed to warm to room temperature and stand for 8 days, at which time its viscosity was measured and found to be 2962 cps at 20° C. The reaction mixture was placed under a vacuum of 1 mm Hg for 3 hours in order to remove dissolved hydrogen chloride, yielding 487 g of product having an index of refraction of 1.5051 at 25° C.

Dentin Primer

The above-described reaction product was used as the first part of a two-part dentin primer composition. The second part of such composition was a solution of three weight percent sodium benzene sulfinate and 0.15% weight percent 2-chlorothioxanthone dissolved in absolute ethanol. Adhesion of the dentin primer composition to unetched dentin was evaluated using the following procedure. Six bovine teeth of similar age and appearance were partially embedded in circular acrylic disks. The exposed portion of each tooth was ground flat and parallel to the acrylic disk using 120 grit silicon carbide paper-backed abrasive mounted on a lapidary wheel, in order to expose the tooth dentin. During this and subsequent grinding and polishing steps, the teeth were continuously rinsed with water. Further grinding and polishing of the teeth was carried out by mounting 400 grit silicon carbide paper-backed abrasive and then 600 grit silicon carbide paper-backed abrasive on the lapidary wheel. The polished teeth were stored in distilled water.

The teeth were then dried under a stream of compressed air. One drop of each part of the above two-part dentin primer composition was placed in a plastic mixing well. The drops were mixed together with a brush for about 10 seconds, painted onto the polished tooth surface, and blown lightly with compressed air. A previously prepared "Teflon" mold having a five mm diameter hole lined with a gelatin sleeve was claimed onto the tooth so that the central axis of the hole in the mold was normal to the polished, primer-coated tooth surface. The cavity in the mold was filled with a visible light-cure microfilled dental restorative ("Silux" brand Universal paste, commercially available from 3M), and cured with a visible light curing light ("Elipar" light, commercially available from Espe Dental Products) for 20 seconds. The tooth and mold were allowed to stand for about 10 minutes at room temperature. The mold was then carefully removed from the tooth, leaving a molded restorative button attached to the primer layer. The disk-tooth-primer-restorative combination was stored in distilled water at 37° C. for 24 hours.

Adhesion of the dentin primer composition to the polished, unetched bovine dentin was evaluated by placing the tooth mounting disk in a holder and clamping the holder in the jaws of an "Instron" apparatus with the primer layer parallel to the direction of pull. A loop of orthodontic wire (0.44 mm diameter) was placed around the restorative button adjacent to the polished tooth surface. The ends of the orthodontic wire were clamped in the pulling jaws of the Instron apparatus, thereby placing the primer bond in shear stress. At a crosshead speed of two mm/min, the average measured shear strength of the primer-dentin bond was 49.3 kg/cm$^2$.

Using the above technique, the primer bond strength on polished bovine enamel (etched for one minute with 37% orthophosphoric acid) was also evaluated. The average measured shear strength of the primer-etched enamel bond was 190.6 kg/cm$^2$.

The above tests were repeated, with addition of two weight percent (based on the weight of the first part) benzoyl peroxide to the first part of the two-part dental primer composition. The average measured shear strength of the primer-dentin bond rose to 62.3 kg/cm$^2$, and the average measured shear strength of the primer-etched enamel bond was 188.7 kg/cm$^2$.

For comparison purposes, a two-part chemical cure dentin primer was prepared. The first part contained the phosphorus-containing polymerizable monomer reaction product described above, along with two weight percent benzoyl peroxide. The second part contained three weight percent sodium benzene sulfinate and one weight percent dihydroxyethyl para-toluidine. When evaluated as described above, the chemical cure dentin primer had an average measured primer-dentin shear strength of 40 kg/cm$^2$ and an average measured primer-etched enamel shear strength of 144 kg/cm$^2$. Thus, the light-curable dentin primer of the invention provides significantly increased adhesion to dentin and enamel, especially when a peroxide compound is added to compositions of the invention.

EXAMPLE 2

Two-Step Curing Method

The peroxide-containing composition of the invention shown in Example 1 was applied and tested as in Example 1, but was cured after application of the composition to teeth and before application and cure of restorative, by exposing the dentin primer-coated teeth to visible radiation from the curing light for 20 seconds.

The dentin primer was converted to a hard, slightly tacky film. "Silux" restorative was applied to the hardened film using the mold described in Example 1, followed by further curing of the restorative using the cure light for 20 seconds. Shear strength was measured as in Example 1. The average measured shear strength of the primer-dentin bond was 86.5 kg/cm$^2$, with some individual test samples exceeding 100 kg/cm$^2$. During shear testing, chunks of dentin were torn from several of the teeth, indicating that the bond strength exceeded the cohesive strength of dentin.

EXAMPLE 3

Thermal Cycling

The composition of the invention shown in Example 2 was evaluated for resistance to thermal cycling. Six samples of the dentin primer composition prepared and applied to unetched dentin as described in Example 2 were thermally cycled between 5° and 45° C. for 500 cycles. When the samples were evaluated as in Example 1, the average measured shear strength values were within 0.5 kg/cm$^2$ of the average values of Example 2. This example indicates that compositions of the invention have excellent hydrolytic and thermal stability.

EXAMPLE 4

Stability

The composition of the invention shown in Example 2 was stored at 45° C. for four weeks. When the stored composition was mixed and evaluated as in Example 2, the average measured shear strength values were within five kg/cm$^2$ of the average values of Example 1.

The composition of the invention shown in Example 2 was placed under a dental operatory light ("Ritter Model K" commercially available from Sybron Corp.) at a distance of 80 cm from the lamp. Detectable evidence of polymerization occurred after about three minutes. Under comparable conditions, typical commercially available visible light cure restoratives harden in about one minute.

This example indicates that the compositions of the invention have very good shelf stability and ambient light tolerance.

EXAMPLES 5–28

Adhesion of Other Compositions of the Invention to Unetched Dentin

Using the method of Examples 1 and 2, different types and amounts of polymerizable monomer, sulfur compound, and photoinitiator were combined and evaluated with and/or without a peroxide compound. Set out below in Table I are the Example number, polymerizable monomer, sulfur compound (and weight percent of sulfur compound in the second part of the composition, based on the weight of the second part), photoinitiator (and weight percent of photoinitiator in the second part of the composition, based on the weight of the second part), peroxide compound, if used (and weight percent of peroxide compound in the first part of the composition, based on the weight of the first part) and the average measured shear strength of the resulting dentin primer compositions when applied to unetched dentin and cured using a one-step or two-step curing method.

TABLE I

| Example Number | Polymerizable monomer | Sulfur compound (weight %) | Photoinitiator (weight %) | Peroxide Compound (weight %) | Bond Strength, kg/cm$^2$ One-step | Two-step |
|---|---|---|---|---|---|---|
| 5 | Example 1 | Example 1 (3) | acetophenone (0.15) | [1]BP[a] (2) | 70.0 | 61.5 |
| 6 | Example 1 | Example 1 (3) | chalcone (0.15) | BP (2) | — | 81.2 |
| 7 | Example 1 | Example 1 (3) | benzophenone (0.15) | BP (2) | — | 65.0 |
| 8 | Example 1 | Example 1 (3) | fluorenone (0.15) | BP (2) | 84.0 | 71.8 |
| 9 | Example 1 | Example 1 (3) | fluorenone (0.15) | — | — | 60.6 |
| 10 | Example 1 | Example 1 (3) | anthrone (0.15) | BP (2) | — | 76.9 |
| 11 | Example 1 | Example 1 (3) | benzanthrone (0.15) | BP (2) | — | 65.1 |
| 12 | Example 1 | Example 1 (3) | 1-chloroanthraquinone (0.15) | BP (2) | 70.7 | 78.9 |
| 13 | Example 1 | Example 1 (3) | 1-chloroanthraquinone (0.15) | — | — | 55.7 |
| 14 | Example 1 | Example 1 (3) | thioxanthone (0.15) | BP (2) | 69.3 | 73.5 |
| 15 | Example 1 | Example 1 (3) | thioxanthone (0.15) | — | 28.8 | 59.7 |
| 16 | Example 1 | Example 1 (3) | 2-isopropylthioxanthone (0.15) | BP (2) | 73.7 | 85.0 |
| 17 | Example 1 | Example 1 (3) | 2-isopropylthioxanthone (0.15) | — | 58.9 | 60.1 |
| 18 | Example 1 | Example 1 (3) | 2-trifluoromethylthioxanthone (0.15) | BP (2) | — | 73.8 |
| 19 | Example 1 | Example 1 (3) | 2-nitrothioxanthone (0.15) | BP (2) | — | 82.9 |
| 20 | Example 1 | Sodium para-toluene sulfinate (3) | 2-chlorothioxanthone (0.15) | BP (2) | — | 79.7 |
| 21 | Example 1 | Example 1 (1.5) | 2-chlorothioxanthone (0.075) | BP (2) | — | 79.9 |
| 22 | Example 1 | Example 1 (3) | 2-chlorothioxanthone-10,10 dioxide (0.15) | BP (2) | — | 85.6 |
| 23 | Example 1 | Example 1 | 2-chloroxanthone | BP | 76.5 | 73.0 |

TABLE I-continued

| Example Number | Polymerizable monomer | Sulfur compound (weight %) | Photoinitiator (weight %) | Peroxide Compound (weight %) | Bond Strength, kg/cm² One-step | Two-step |
|---|---|---|---|---|---|---|
| 24 | Example 1 | Example 1 (3) | 2-chloroxanthone (0.15) | — | 62.2 | 63.5 |
| 25 | Example 1 | Example 1 (3) | 10-methyl-9(10H)acridone (0.15) | BP (2) | 70.5 | 76.6 |
| 26 | Example 1 | Example 1 (3) | 10-methyl-9(10H)acridone (0.15) | — | — | 69.8 |
| 27 | "Clearfil" resin[b] | Example 1 (3) | 2-chlorothioxanthone (0.15) | BP (2) | 35.0 | 80.1 |
| 28 | "Sankin" resin[c] | para-toluene sulfinic acid (5) | 2-chlorothioxanthone (0.15) | BP (1) | — | 21.2 |

[a] Benzoyl peroxide
[b] "Clearfil Bond System F" catalyst liquid (commercially available from Kuraray Co., Ltd.), believed to contain two weight percent benzoyl peroxide in a mixture of monomers including 2-methacryloxyethyl phenyl phosphate, BIS-GMA and triethyleneglycol dimethacrylate.
[c] "Sankin" catalyst liquid (manufactured by Sankin Kogyo Co.), believed to contain one weight percent benzoyl peroxide in $[[CH_2=C(CH_3)COOC_2H_4O]_2P(O)]_2O$.

These examples show the use of a variety of types and amounts of free-radically polymerizable monomers, sulfur compounds, and photoinitiators in compositions of the invention, with and without a peroxide compound and with one-step and two-step cure methods. Many of these compositions exhibit exceptional increases in bond strength when two-step and one-step cure methods are compared.

COMPARISON EXAMPLE

The effect of removal of the sulfur compound and its replacement by an amine was demonstrated as follows. The first part of the non-peroxide-containing composition of Example 1 was combined with a second part containing 0.25 weight percent 2-chlorothioxanthone and 0.5 weight percent diethylaminoethyl methacrylate in absolute ethanol. When the resulting composition was evaluated as in Example 1, the average measured shear strength of the primer-dentin bond was 18.9 kg/cm², a value only 38 percent of the value obtained (49.3 kg/cm²) for the sulfur compound-containing composition of Example 1.

In a second comparison, the first part of the non-peroxide-containing composition of Example 9 was combined with a second part containing 0.5 weight percent fluorenone and 0.5 weight percent diethylaminoethyl methacrylate in absolute ethanol. When the resulting composition was evaluated as in Example 9, the average measured shear strength of the primer-dentin bond was 5.2 kg/cm², a value only 9 percent of the value (60.6 kg/cm²) obtained for the sulfur compound-containing composition of Example 9.

Various modifications and alterations of this invention will become apparent to those skilled in the art without departing from the scope and spirit of this invention, and it should be understood that this invention is not limited to the illustrative embodiments set forth herein.

We claim:
1. A visible light cure dentin and enamel primer composition, comprising:
   (a) as a first component, phosphorous-containing free-radically polymerizable monomer suitable for use in the oral environment;
   (b) as a second component, sulfur compound having sulfur in the +2 or +4 oxidation state, said second component acting as a polymerization activator for said first component and enhancing adhesion of said composition to dentin; and
   (c) as a third component, photoinitiator selected from substituted and unsubstituted alkylphenones, substituted and unsubstituted benzilidene acetophenones, and compounds of the formula:

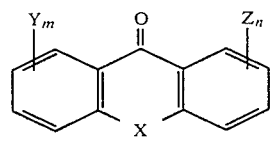

wherein:
X is nothing, a carbon-carbon bond, $CR_2$, $C=^1$, $C=O$, $S$, $SO$, $SO_2$, $O$, or $NR$ where each R is independently H or a lower alkyl or substituted alkyl group and $R^1$ is a tetravalent unsaturated aliphatic radical doubly bonded to said C of $C=R^1$ and bonded to the 4 or 5 position of said Formula I to form a fused ring structure;
Y and Z are independently lower alkyl, substituted alkyl, a divalent unsaturated radical bonded to adjacent positions of said Formula I to form a fused ring structure, alkoxy, halogen, or nitro; and
m and n are independently zero to 4.

2. A composition according to claim 1, wherein said polymerizable monomer contains phosphorus atoms bonded to one or more olefinically unsaturated groups and bonded to one or more chlorine atoms, bromine atoms, active hydrogen atoms, or alkyl, substituted alkyl, allyl, or substituted allyl groups.

3. A composition according to claim 1, wherein said polymerizable monomer comprises an organic ester of one or more acids of phosphorus, the organic radical of said ester containing at least one free-radically polymerizable functional group, and wherein said ester has chlorine or bromine bonded directly to phosphorus.

4. A composition according to claim 1, wherein said polymerizable monomer is selected from
   (a) 2-methacryloxyethyl phenyl phosphate, and
   (b) halophosphorus ester wherein the organic radical of said ester is the residue remaining after removal of one or more hydroxyl hydrogen atoms from BIS-GMA, phosphorus is doubly bonded to an oxygen atom, is bonded to at least one chlorine atom, and the ratio of said phosphorus to said BIS-GMA is between about 0.015:1 and 1:1.

5. A composition according to claim 1, wherein said sulfur compound comprises an alkali metal salt or ammonium salt of a sulfinate, sulfite, sulfonate, bisulfite, metabisulfite, or hydrosulfite anion, or the free acid counterpart thereof.

6. A composition according to claim 1, wherein said sulfur compound comprises sodium benzene sulfinate or para-toluene sulfinate.

7. A composition according to claim 1, wherein said photoinitiator comprises an alkylphenone or a benzilidene acetophenone.

8. A composition according to claim 1, wherein said photoinitiator comprises a compound of said Formula I.

9. A composition according to claim 1, wherein said photoinitiator comprises a xanthone or thioxanthone.

10. A composition according to claim 1, wherein said photoinitiator comprises 2-chlorothioxanthone.

11. A composition according to claim 1, further comprising an acyl or alkyl peroxide or hydroperoxide, or a diacyl or dialkyl peroxide.

12. A composition according to claim 1, further comprising benzoyl peroxide.

13. A composition according to claim 11, wherein said composition is in two parts, the first of said two parts containing said polymerizable monomer and said peroxide or hydroperoxide, the second of said two parts containing said sulfur compound, and either or both of said two parts containing said photoinitiator, and wherein said polymerizable monomer is about 5 to 95 percent by weight of said composition after said two parts are mixed, said sulfur compound is about 0.5 to 10 percent by weight of said polymerizable monomer, and said photoinitiator and said peroxide or hydroperoxide are each independently about 0.05 to 10 percent by weight of said polymerizable monomer.

14. A two-part visible light cure dentin primer, one part of which comprises a peroxide compound and the reaction product of BIS-GMA in a diluent with about 0.25 to 10 percent by weight, based on the weight of said BIS-GMA, of phosphorus oxychloride, and the second part of which is a liquid solution comprising alkali benzene sulfinate and 2-chlorothioxanthone.

15. A two-part visible light cure cavity liner, crown preparation or adhesive, one part of which comprises radioopaque filler, a peroxide compound, and the reaction product of BIS-GMA in a diluent with about 0.25 to 10 percent by weight, based on the weight of said BIS-GMA, of phosphorus oxychloride, and the second part of which is a liquid solution comprising alkali benzene sulfinate and 2-chlorothioxanthone.

* * * * *

UNITED STATES PATENT AND TRADEMARK OFFICE
CERTIFICATE OF CORRECTION

PATENT NO. : 4,544,467  (Page 1 of 3)
DATED : October 1, 1985
INVENTOR(S) : James E. Bunker and Richard P. Fields It is certified that error appears in the above-identified patent and that said Letters Patent is hereby corrected as shown below:

Col. 2, lines 20 and 21

"(e.g., with lower ($C_{1-4}$) alkyl, unsubstituted alkyl, alkoxy, halogen, or nitro) and substituted benzilidene" should read -- (e.g., with lower ($C_{1-4}$) alkyl, substituted alkyl, alkoxy, halogen, or nitro) and unsubstituted benzilidene --.

Col. 2, line 32  "(i.e., not bond)" should read -- (i.e., not a bond) --.

Col. 2, line 43  "Formula II" -- should read -- Formula I --.

Col. 3, lines 21 and 22  "state, typically," should read -- state. Typically, --.

UNITED STATES PATENT AND TRADEMARK OFFICE
CERTIFICATE OF CORRECTION

PATENT NO. : 4,544,467 (Page 2 of 3)

DATED : October 1, 1985

INVENTOR(S) : James E. Bunker and Richard P. Fields

It is certified that error appears in the above-identified patent and that said Letters Patent is hereby corrected as shown below:

Col. 4, lines 39 and 40 , "polymerization for" should read -- polymerization activator for --.

Col. 5, line 57 "acyl and acyl peroxides" should read -- acyl and alkyl peroxides --.

Col. 7, line 1 "compositions" should read -- composition --.

Col. 8, line 5 "claimed" should read -- clamped --.

UNITED STATES PATENT AND TRADEMARK OFFICE
CERTIFICATE OF CORRECTION

PATENT NO. : 4,544,467 (Page 3, of 3)
DATED : October 1, 1985
INVENTOR(S) : James E. Bunker and Richard P. Fields It is certified that error appears in the above-identified patent and that said Letters Patent is hereby corrected as shown below:

Cols. 9 and 10, Table I, first row of the table, under the column labelled "Peroxide Compound", "$^{11}BP^a$" should read -- $BP^a$ --.

Col. 12, line 34 "$C=^1$," should read -- $C=R^1$ --.

Signed and Sealed this

Tenth Day of June 1986

[SEAL]

Attest:

DONALD J. QUIGG

*Attesting Officer* *Commissioner of Patents and Trademarks*